United States Patent [19]

Ong et al.

[11] 4,198,419

[45] Apr. 15, 1980

[54] PHENYLTHIOPHENYLPIPERIDINES

[75] Inventors: Helen H. Ong, Whippany; James A. Profitt, Somerville, both of N.J.

[73] Assignee: American Hoechst Corporation, Bridgewater, N.J.

[21] Appl. No.: 2,349

[22] Filed: Jan. 10, 1979

[51] Int. Cl.$^2$ .................. A61K 31/445; C07D 211/64
[52] U.S. Cl. ..................................... 424/267; 546/207; 546/214; 546/215; 546/226; 546/225; 546/228
[58] Field of Search ............... 546/207, 214, 215, 225, 546/226, 228; 424/267

[56] References Cited

U.S. PATENT DOCUMENTS 4,066,654  1/1978  Adelstein et al. .................... 546/228

*Primary Examiner*—Alan L. Rotman
*Assistant Examiner*—Robert T. Bond
*Attorney, Agent, or Firm*—Curtis, Morris & Safford

[57] ABSTRACT

Novel phenylthiophenylpiperidines and methods of preparing same are described. These compounds are useful as analgetics, antidepressants, anticonvulsants and intermediates for preparing other pharmaceutically active compounds.

73 Claims, No Drawings

PHENYLTHIOPHENYLPIPERIDINES

This invention relates to novel phenylthiophenylpiperidines and pharmaceutically acceptable acid addition salts thereof which are useful as analgetics, antidepressants and anticonvulsants, to methods of treatment with pharmaceutically effective amounts thereof and to pharmaceutical compositions containing such compounds as essential active ingredients. Additionally, the compounds of this invention are useful as intermediates in the preparation of more active compounds of this invention and other pharmaceutically active compounds described in our application filed on even date herewith and entitled "Spiro[dibenz[b,f]thiepin-piperidine]s." The phenylthiophenylpiperidines have the formula

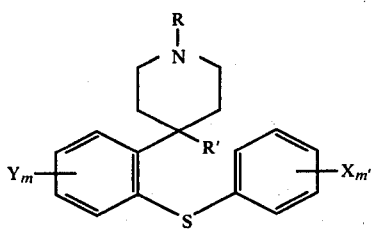

in which R is hydrogen, loweralkyl, loweralkenyl, loweralkynyl, cycloalkylloweralkyl, phenylloweralkyl, loweralkanoyl, aminocarbonyl, phenoxycarbonyl, benzoylloweralkyl, cyano, ethylene glycol ketal of the formula

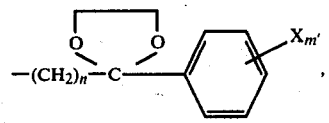

or tetrahydrofurylmethyl; R' is cyano, COOH, COZ, loweralkanoyl or loweralkoxycarbonyl; X and Y are the same or different and each can be hydrogen, chlorine, fluorine, bromine, methoxy, methylthio or trifluoromethyl; Z is chlorine, fluorine or bromine; m and m' are the same or different and each can be the integer 1 or 2; n is an integer of 1 to 4, inclusive.

In the above definitions and throughout, the following have the assigned significance, unless otherwise specified:

"lower" means the particular group described thereby contains up to and including 5 carbon atoms and can be straight or branched chain;

"ambient" means the temperature is that of its natural surroundings, i.e., room temperature or about 15°–30° C.;

"cycloalkyl" contains between 3 and 7, inclusive, carbon atoms;

"phenyl" or "phenyl derivative" (e.g. benzoyl) means the particular phenyl ring can contain one or more of the following: nitro, amino, chlorine, fluorine, bromine, methoxy, loweralkyl or trifluoromethyl;

Acids useful for preparing the pharmaceutically acceptable acid addition salts of the present invention include inorganic acids such as hydrochloric, hydrobromic, sulfuric, nitric, phosphoric and perchloric acids, as well as organic acids such as tartaric, citric, acetic, succinic, maleic, fumaric and oxalic.

To the best of our knowledge the compounds of the present invention have not heretofore been described or suggested.

The compounds of the present invention are useful as analgetics due to their ability to alleviate pain in mammals, as demonstrated in the phenyl-2-quinone writhin assay in mice, a standard assay for analgesia [Proc. Soc. Exptl. Biol. Med., 95, 729 (1957)].

Compounds of the present invention are also useful for the treatment of depression in mammals, as demonstrated by their ability to inhibit tetrabenazine-induced depression in mice [International Journal of Neuropharmacology, 8, 73 (1969)], a standard assay for useful antidepressant properties.

Compounds of the present invention are further useful as anticonvulsant agents for mammals, as determined by the method of Woodbury, L. A. and Davenport, V. D. [Arch., Int. Pharmacodynam, 92, pp 97–107 (1952)].

The compounds of the invention have the utilities described above when administered in amounts ranging from 0.1 to about 100 mg/kg of body weight per day.

Compounds of this invention include:
1-ethyl-4-(ethylcarbonyl)-4-(2-phenylthiophenyl)-piperidine;
4-acetyl-1-ethyl-4-(2-phenylthiophenyl)piperidine;
1-methyl-4-[2-(2-trifluoromethyl)phenylthiophenyl]-piperidine-4-carboxylic acid;
4-acetyl-1-cyclohexylmethyl-4-(2-phenylthiophenyl)-piperidine;
4-[2-(3,4-dichlorophenylthio)phenyl]-4-cyanopiperidine;
4-acetyl-4-[2-(2,3-dibromo-4-fluorophenylphenylthio)-phenyl]piperidine;
4-[2-(4-bromo-2,3-dichlorophenylthio)phenyl]-4-(ethylcarbonyl)piperidine;
1,4-dicyano-4-[2-(2,3-dichloro-4-trifluoromethyl)-phenylthiophenyl]piperidine;
4-acetyl-1-[4-(4-fluorobenzoyl)-n-butyl]-4-(2-phenyl-thiophenyl)piperidine;
4-acetyl-1-[2-(4-fluorobenzoyl)ethyl]-4-(2-phenylthiophenyl)piperidine;
1-(2-butynyl)-4-(ethylcarbonyl)-4-(2-phenylthiophenyl)piperidine;
4-acetyl-1-allyl-4-[2-(4-chlorophenylthio)-5-fluorophenyl]piperidine;
4-ethylcarbonyl-4-[2-(4-fluorophenylthio)-4-methoxyphenyl]-1-dimethylallylpiperidine;
4-[5-bromo-2-(4-methylthiophenylthio)phenyl]-4-ethoxycarbonyl-1-dimethylallyl piperidine;
4-acetyl-1-allyl-4-[2-(4-bromophenylthio)-4,5-dichlorophenyl]piperidine;
1-allyl-4-ethylcarbonyl-4-[2-(4-trifluoromethylphenylthio)-5-methylthiophenyl]piperidine;
1-dimethylallyl-4-[2-(4-methoxyphenylthio)-5-trifluoromethyl]-piperidine-4-carboxylic acid;
1-acetyl-4-(2-phenylthiophenyl)piperidine-4-carbonyl bromide; and
1-acetyl-4-(2-phenylthiophenyl)piperidine-4-carbonyl fluoride.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form ad may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; anti-bacterial agents such as benzyl alcohol or methyl paraben; antioxidants such as ascorbic acid or sodium bisulfite; chelating agents such as ethylene diamine tetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The compounds of the invention can be prepared according to one or more of the following methods in which R, R', X, Y, Z and m, unless otherwise indicated, are as defined above and R'' is lower alkyl.

METHOD A

A 2-phenylthiophenylacetonitrile of the formula

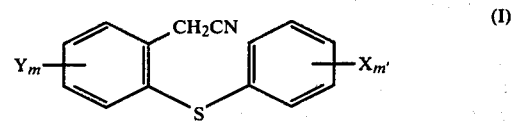

is subjected to bisalkylation with mechlorethamine hydrochloride in the presence of a strong base at a temperature ranging from ambient to about 85° C. to provide the corresponding 4-cyano-1-methyl-4-(2-phenylthiophneyl)piperidine of the formula

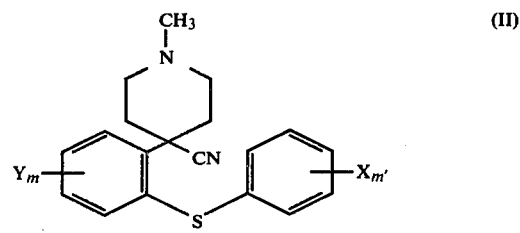

Preferred methods include the use of dimethylformamide or dimethylsulfoxide as solvent and sodium hydride as the strong base.

METHOD B

A compound of formula II is treated according to the first step of the von Braun reaction to provide the corresponding 1,4-dicyano-4-(2-phenylthiophenyl)piperidine of the formula

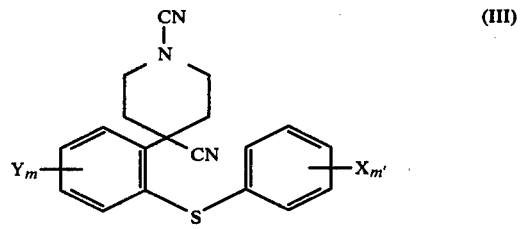

A solvent such as chloroform or methylene dichloride, a mild acid scavenger such as potassium carbonate and a reaction temperature ranging from about ambient to reflux of the reaction mixture are suitable for the reaction.

METHOD C

A compound of formula III is subjected to acid hydrolysis to provide the corresponding 4-(2-phenylthiophenyl)-piperidine-4-carboxylic acid of the formula

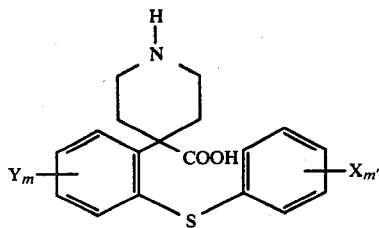

(IV)

A preferred method utilizes concentrated (48%) hydrobromic acid or a mixture of concentrated hydrobromic acid and glacial acetic at temperatures ranging from about 100° C. to reflux.

METHOD D

A compound of formula IV is acylated in the presence of an acid scavenging medium, to provide the corresponding 1-alkanoyl-4-(2-phenylthiophenyl)-piperidine-4-carboxylic acid of the formula

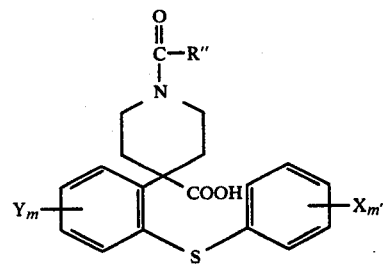

(V)

It is preferred to utilize pyridine as an acid scavenging medium. Also, an appropriate acyl halide, for example, acetyl chloride, or acyl anhydride, e.g., acetic, can be the acylating agent.

METHOD E

A compound of formula V is carefully subjected to displacement with thionyl halide to provide the corresponding acid of the formula

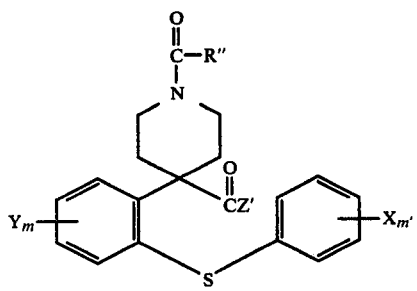

(VI)

A preferred method utilizes thionyl chloride with the displacement carried out by heating on a steam bath for about 5 minutes.

METHOD F

A compund of formula II is treatd with a Grignard reagent of the formula R"Mghal, in which R" is straight or branched chain loweralkyl and hal is bromine or chlorine, under Grignard reaction conditions to provide the corresponding 4-alkylcarbonyl-4-(2-phenylthiophenyl)piperidine depicted by the formula

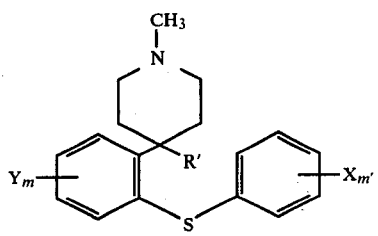

(VII)

in which R' is loweralkanoyl. Preferred reaction conditions include a solvent such as ether or tetrahydrofuran and temperatures ranging from about 15° C. to reflux of the reaction mixture.

METHOD G

A compound of formula VII is treated according to the procedure of Method B to provide the corresponding N-cyano compound depicted by the formula

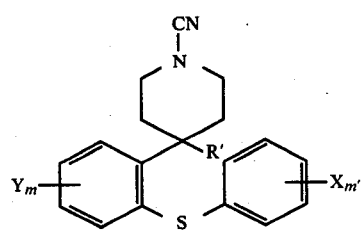

(VIII)

in which R' is loweralkanoyl.

METHOD H

A compound of formula III or VIII is subjected to hydrolysis to remove the N-cyano group to provide a compound depicted by the formula

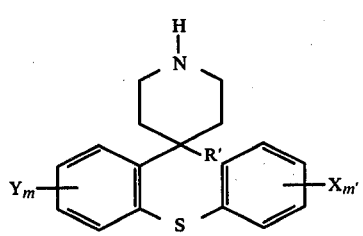

(IX)

in which R' is cyano or loweralkanoyl. Preferred conditions include the use of a mild acid such as 2 N hydrochloric acid or a mixture of 2-3 N hydrochloric acid and glacial acetic acid and an elevated temperature ranging from about 90° C. to reflux of the reaction mixture.

METHOD I

A compound of formula VI is subjected to esterification with simultaneous cleavage of the amide bond by refluxing in the presence of an acid saturated alcohol of the formula R"OH, in which R" is straight or branched chain alkyl, to provide the corresponding 4-alkoxycarbonyl-4-(2-phenylthiophenyl)piperidine of the formula

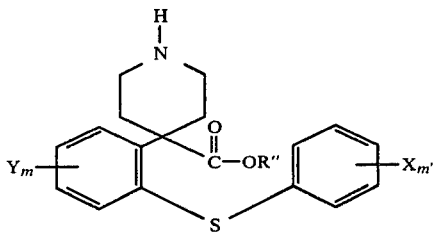

(X)

METHOD J

A compound of formula IX or X is alkylated with an appropriate alkylating agent by any convenient method known to the art to provide the corresponding N-substituted compound of the formula

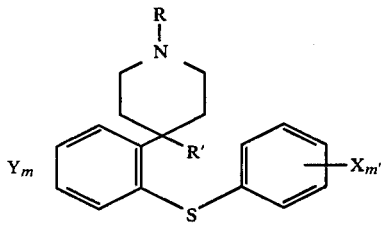

(XI)

in which R is loweralkyl, loweralkenyl, loweralkynyl, tetrahydrofurylmethyl, cycloalkylloweralkyl, phenylloweralkyl or ethylene glycol ketal of the formula

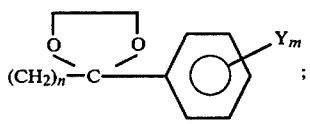

and R' is loweralkanoyl or loweralkoxycarbonyl. A preferred method includes the use of dimethylformamide as a solvent, sodium bicarbonate as an acid scavenger and a reaction temperature of from 50°–90° C. Optionally, a reaction initiator, preferably potassium iodide, may be used.

METHOD K

An ethylene ketal compound of formula XI is subjected to acid hydrolysis to provide the corresponding compound in which R is benzoylloweralkyl $$-(CH_2)_m\overset{O}{\underset{\|}{C}}-\underset{}{\underset{}{\bigcirc}}-Y .$$

3 N hydrochloric acid in ethanol is preferred as the agent effecting hydrolysis.

METHOD L

A compound of formula XI in which R' is COOR" is hydrolyzed by any convenient method known to the art to provide the corresponding compound in which R is COOH. The use of dilute sodium hydroxide is preferred.

METHOD M

A compound obtained in any of the above methods in which R is not H and R' is COOH is esterified by any convenient method known to the art to provide the corresponding compound in which R' is $$\overset{O}{\underset{\|}{-C}}-O-\text{loweralkyl}.$$

In a preferred method the acid precursor is converted to its acid halide which in turn is esterified.

In each of the above methods, optimum conditions depend upon starting materials, solvents, catalysts and other reaction components. This will become more apparent in the examples given below.

Starting materials depicted by equation 1 are either commercially available or can be prepared by routine methods according to the following sequence of reactions:

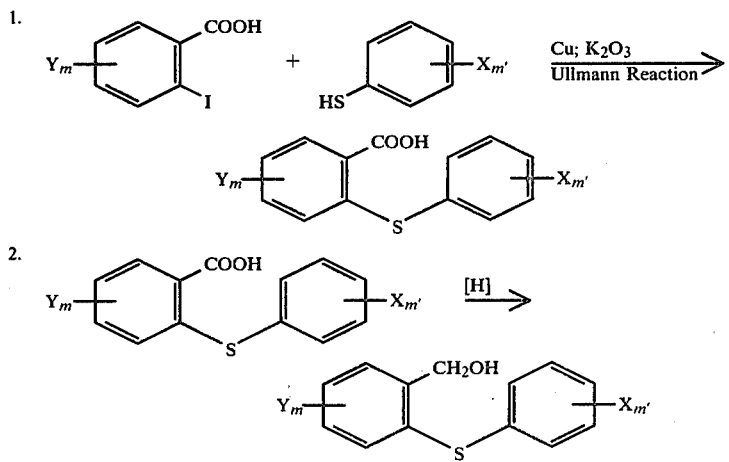

[reduction with sodium-bis-(2-methoxyethoxy)aluminum hydride (VITRIDE$^R$)]

3.

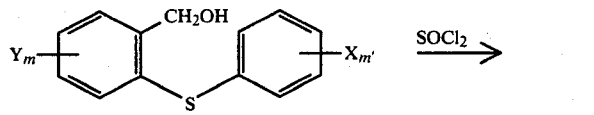

4.

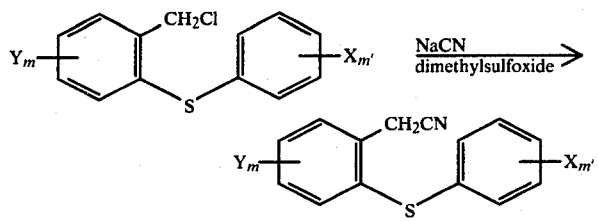

(I)

The invention is further illustrated by the following specific examples.

EXAMPLE 1

2.8 g of 99% sodium hydride are added portionwise over a 5 minute span to a solution, under nitrogen, of 6.0 g of 2-(4-chlorophenylthio)benzyl cyanide in 36 ml of dimethylsulfoxide. After total addition, the reaction mixture is stirred for 4 minutes before adding portionwise over a 35 minute span a solution of 4.7 g of 95% mechlorethamine hydrochloride in 24 ml of dimethylsulfoxide. Thereafter, the reaction mixture is heated at 70°–80° C. for 80 minutes and then permitted to cool to ambient temperature. The cooled mixture is poured onto 175 ml of ice and the aqueous mixture is extracted thrice with 75 ml portions of ether. The combined ether extracts are washed thrice with 50 ml portions of water and then extracted with 40 ml of 2 N hydrochloric acid. The white salt is collected by filtration and successively washed with water, washed with ether and dried. The solid is recrystallized from acetone and then twice from a methyl alcohol-ether mixture to provide the product, mp 257°–259° C., of 4-[2-(4-chlorophenylthio)phenyl]-4-cyano-1-methylpiperidine hydrochloride.

EXAMPLE 2

A mixture of 6.3 g of 4-[2-(4-chlorophenylthio)-phenyl]-4-cyano-1-methylpiperidine hydrochloride, Example 1, in 26 ml of 48% hydrobromic acid is stirred in a 135°–140° C. bath for 60 hours before 13 ml of glacial acetic acid is added. The reaction mixture is maintained at this temperature for 24 hours while stirring is continued. Thereafter, the mixture is diluted with 250 ml of water and the diluted mixture is rotary evaporated in a 90° C. bath.

This dilution and evaporation process is repeated twice and the final residue is taken up in 50 ml of water and then 5 ml of a 58% ammonium hydroxide solution is added precipitating a white powder. The powder is collected, washed with acetone and recrystallized from methyl alcohol to give the pure product, mp 284°–285° C., of 4-[2-(4-chlorophenylthio)phenyl]-1-methylpiperidine-4-carboxylic acid.

EXAMPLE 3

2.6 g of 99% sodium hydride are added portionwise to a solution of 4.4 g of 2-(phenylthio)phenylacetonitrile in 50 ml of dimethylformamide. The resulting reddish brown mixture is stirred for 30 minutes before adding dropwise a solution of 4.0 g of mechlorethamine hydrochloride in 50 ml of dimethylformamide, maintaining gas evolution at a slow rate. After total addition, the mixture is stirred at 80°–85° C. for 15 hours. Thereafter, 100 g of ice are added before the mixture is extracted thrice with ether. The combined ether extracts are dried over potassium carbonate and then the solvent is removed under vacuum leaving a brownish oil. The oil is dissolved in a small amount of ether and passed through, with additional ether, an alumina column which is packed in ether. The effluent is concentrated leaving an oil which is converted to its hydrochloride which is recrystallized from an acetone-ether mixture, leaving 4-cyano-1-methyl-4-(2-phenylthiophenyl)-piperidine hydrochloride.

Analysis: Calculated for $C_{19}H_{20}N_2O \cdot HCl$: 69.41%C; 6.42%H; 8.52%N; 10.78%Cl. Found: 69.59%C; 6.57%H; 8.62%N; 10.90%Cl.

EXAMPLE 4 a. A mixture of 147 g of iodobenzoic acid, 45.5 g of potassium carbonate in 57 ml of nitrobenzene is maintained with stirring at 160° C. for 40 minutes. Thereafter, 46.5 g of additional potassium carbonate which is followed by the addition of 73.1 g of 4-fluorothiophenol, another 46.5 g of potassium carbonate and 0.35 g of copper powder. The reaction mixture is stirred in a 160° C. bath for 45 minutes. The resulting solid is collected and then cooled to 0° C. before being mixed with 100 ml of water and 220 ml of 6 N hydrochloric acid. The aqueous mixture is then diluted to 1 liter total volume before being stirred with 450 ml of chloroform. The resulting white solid is collected and washed successively with chloroform and water. The solid is dissolved in hot acetone and the acetone solution is successively filtered and cooled to provide a white crystalline product. The product is recrystallized from acetone and then converted to a salt with potassium carbonate. The salt is dissolved in water and the aqueous solution acidified with 1 N hydrochloric acid to provide 2-(4-fluorophenylthio)benzoic acid.

b. 36.1 ml of 70% sodium-bis-(2-methoxyethoxy)aluminum hydride in benzene are added dropwise over a one hour span to a stirring mixture of 15 g of 2-(4-fluorophenylthio)benzoic acid in 150 ml of benzene under nitrogen at ambient temperature. After total addition, the reaction mixture is stirred for an additional 30 minutes and then permitted to stand for 4 days. Thereafter, the reaction mixture is cooled to 0° C. before 100 mls of 10% sodium hydroxide are added with stirring. Following this addition, the layers separate and the aqueous layer is extracted twice with 100 ml portions of benzene. The combined benzene solutions are successively washed twice with 100 ml portions of water, washed once with a 60 ml portion of a saturated sodium chloride solution and dried, providing a clear yellow oil. The oil is distilled at 118.5°–121.5° C. and 0.07 mm pressure to provide a clear, colorless liquid, 2-(4-fluorophenylthio)benzyl alcohol.

c. 8.5 g of thionyl chloride are added dropwise over a 10 minute span to a stirring mixture of 13.0 g of 2-(4-fluorophenylthio)benzyl alcohol in 80 ml of benzene at ambient temperature. After total addition, the reaction mixture is stirred for 16 hours before being carefully poured onto 350 ml of crushed ice containing 8 g of sodium bicarbonate. The mixture is stirred until the ice melts. The layers separate and the benzene layer is successively washed twice with 40 ml portions of a half saturated sodium bicarbonate solution, washed twice with 40 ml portions of water, washed once with 25 ml of saturated sodium chloride solution, dried and rotary evaporated to provide 2-(4-fluorophenylthio)benzyl chloride.

d. 12.0 g of 2-(4-fluorophenylthio)benzyl chloride are added portionwise over a 30 minute span to a mixture of 2.9 g of sodium cyanide in 120 ml of dimethylsulfoxide. After total addition, the reaction mixture is stirred for 26 hours before being poured onto 150–200 ml of crushed ice. The mixture is extracted four times with 70 ml portions of ether and the combined ether extracts are successively washed four times with 50 ml portions of water, washed once with 25 ml of saturated sodium chloride solution and dried, providing 2-(4-fluorophenylthio)benzyl cyanide.

e. 2.3 g of 99% sodium hydride are slowly added to a mixture, under nitrogen, of 4.3 g of 2-(4-fluorophenylthio)-benzyl cyanide in 30 mls of dimethylsulfoxide. After total addition, the mixture is stirred for an additional five minutes and then a mixture of 3.9 g of 95% mechlorethamine hydrochloride in 20 ml of dimethylsulfoxide is added portionwise over a 40 minute span. After this addition, the reaction is stirred for 1 hour in a hot water bath at 70° C. and then permitted to stand at ambient temperature for 16 hours. The cooled reaction mixture is poured onto 150 ml of crushed ice and the diluted mixture is extracted thrice with 60 ml portions of ether. The combined ether extracts are washed with 25 ml of saturated sodium chloride solution and dried, leaving a solid. The solid is recrystallized from cyclohexane, leaving the pure product, 4-cyano-4-[2-(4-fluorophenylthio)phenyl]-1-methylpiperidine.

EXAMPLE 5

A solution of 2 g of 4-cyano-1-methyl-4-(2-phenylthiophenyl)piperidine, free base of Example 3, in 25 ml of ether is added dropwise with vigorous stirring to 5 ml of ethylmagnesium bromide. After total addition, stirring is continued for 16 hours. Thereafter, saturated aqueous ammonium chloride is added to decompose the reaction mixture. The ether solution is separated and then successively extracted thrice with 10 ml portions of 2 N hydrochloric acid, warmed on a steam bath and potassium carbonate is added. The resulting amine is dissolved in ether. The ether solution is dried and evaporated off. The resulting solid is purified by column chromatography (alumina column, 5% methanol in methylene chloride eluant). The purified product is converted, in ether, to its oxalic acid salt. The salt is recrystallized from a methyl alcohol-ether mixture to provide 4-ethylcarbonyl-1-methyl-4-(2-phenylthiophenyl)-piperidine oxalate.

EXAMPLE 6

A solution of 2.5 g of 4-cyano-1-methyl-4-(2-phenylthiophenyl)piperidine, free base of Example 3, in 10 ml of tetrahydrofuran is added dropwise to 15 ml of methylmagnesium bromide in ether (2.5 M). After total addition, the reaction mixture is refluxed for 3 days and then decomposed with an excess of saturated ammonium chloride. The organic layer is separated and extracted four times with 10 ml portions of 2 N hydrochloric acid. The acidic solution is warmed on a steam bath for 1 hour before adding potassium carbonate. The resulting product is shaken into ether and the ethereal solution is evaporated to dryness, leaving a crude product. This product is purified by column chromatography (alumina column, and a 5% methyl alcohol in methylene chloride eluant) and then converted, in ether, to its oxalic acid salt. The salt is recrystallized from an ethyl alcohol-ether mixture to give 4-acetyl-1-methyl-4-(2-phenylthiophenyl)piperidine oxalate.

EXAMPLE 7

A solution of 2 g of 4-cyano-1-methyl-4-(2-phenylthiophenyl)piperidine, free base of Example 3, in 16 ml of tetrahydrofuran is added dropwise to a Grignard reagent prepared from 5.93 g of n-propyl iodide, 0.9 g of magnesium and 30 ml of ether. After total addition, the reaction mixture is stirred at reflux for 4 days. Thereafter, the mixture is decomposed with an excess of ammonium chloride followed by mild acid hydrolysis, providing a crude product. The product is purified by column chromatography (alumina column—a 5% methyl alcohol in methylene chloride mixture as eluant) and then converted, in ether, to its oxalic acid salt. The salt is recrystallized from a methyl alcohol-acetone-ether mixture to provide 1-methyl-4-(2-phenylthiophenyl)-4-propylcarbonylpiperidine oxalate.

EXAMPLE 8

A solution of 6.8 g of 4-acetyl-1-methyl-4-(2-phenylthiophenyl)piperidine oxalate, Example 6, in 40 ml of chloroform is added dropwise to a rapidly stirring mixture of 14.7 g of potassium carbonate and 3.7 g of cyanogen bromide in 48.5 ml of chloroform. After total addition, the reaction mixture is successively stirred at reflux for 16 hours, filtered, washed five times with 100 ml portions of water, washed with one 50 ml portion of a saturated sodium chloride solution and dried. The resulting product is purified by chromatography (silica gel column, ether eluant) to provide 4-acetyl-1-cyano-4-(2-phenylthiophenyl)piperidine.

EXAMPLE 9

A solution of 4.8 g of 4-acetyl-1-cyano-4-(2-phenylthiophenyl)piperidine, Example 8, in 50 ml of 2 N hydrochloric acid is refluxed for 16 hours, effecting a white precipitate. The precipitate is collected by filtration and then washed twice with 50 ml portions of water and dried, providing 4-acetyl-4-(2-phenylthiophenyl)piperidine hydrochloride.

EXAMPLE 10

A solution of 3.2 g of 4-ethylcarbonyl-1-methyl-4-(2-phenylthiophenyl)piperidine, free base of Example 5 in 300 ml of chloroform is added portionwise over a 10 minute span to a refluxing mixture of 7.5 g of potassium carbonate and 2.0 g of cyanogen bromide in 30 ml of chloroform. After total addition, stirring is continued at reflux for two additional hours. Thereafter, the mixture is filtered and the filtrate is concentrated to dryness, leaving an oil residue. The residue is taken up in about 50 ml of ethyl alcohol and the alcoholic solution is heated on a steam bath for 5–10 minutes before evaporating off the solvent. The resulting oil solidifies on standing and the solid is recrystallized from a benzene-hexane mixture to provide 1-cyano-4-ethylcarbonyl-4-(2-phenylthiophenyl)-piperidine.

EXAMPLE 11

A suspension of 2.8 g of 1-cyano-4-ethylcarbonyl-4-(2-phenylthiophenyl)piperidine, Example 10 in 30 ml of 3 N hydrochloric acid is stirred at reflux for 16 hours. The resulting crystalline product is successively collected by filtration, dried and recrystallized from a methyl alcohol-ether mixture to provide shiny plates, mp 296°–297° C. (dec), of 4-ethylcarbonyl-4-(2-phenylthiophenyl)piperidine hydrochloride.

EXAMPLE 12

A mixture of 2.03 g of 4-ethylcarbonyl-4-(2-phenylthiophenyl)piperidine hydrochloride, Example 11, 1.3 g of β-bromoethylbenzene, 3 g of sodium bicarbonate and 2 g of potassium iodide in 15 ml of dimethylformamide is stirred at 70° C. for 16 hours. Thereafter, the mixture is permitted to cool before being diluted with 100 ml of water and 200 ml of ether. Layers separate and the ether solution is dried. The ether is evaporated off leaving a brownish oil which is purified by column chromatography (alumina column, ether eluant). The resulting product is converted to a crystalline hydrobromic acid salt which is recrystallized from an acetone-ether mixture to provide the product, 4-ethylcarbonyl-1-phenethyl-4-(2-phenylthiophenyl)piperidine hydrobromide.

EXAMPLE 13

A solution of 2.6 g of 4-cyano-1-methyl-4-(2-phenylthiophenyl)piperidine, free base of Example 3, in 22 ml of chloroform is added rapidly to a stirred mixture of 1.5 g of cyanogen bromide and 6 g of potassium carbonate in 50 ml of chloroform. Thereafter, the reaction mixture is stirred at reflux for 16 hours and then filtered. The filtrate is concentrated to dryness, leaving an oily residue which is dissolved in a small volume of methyl alcohol in which it is warmed on a steam bath to decompose any unreacted cyanogen bromide. The methyl alcohol is then evaporated off, leaving a pale yellowish residue which solidifies with cooling. The solid is recrystallized from an acetone-hexane mixture to 1,4-dicyano-4-(2-phenylthiophenyl)piperidine.

EXAMPLE 14

A suspension of 8 g of 1,4-dicyano-4-(2-phenylthiophenyl)-piperidine, Example 13, in 120 ml of 48% hydrobromic acid is stirred at reflux for 16 hours. Thereafter, the excess is removed by distillation. The residue is dissolved in 100 ml of water. The aqueous solution quickly becomes cloudy as crystals begin to deposit. The aqueous mixture is cooled at 0° C. for 16 hours before crystals are collected. The crystals are recrystallized from an ethyl alcohol-acetone ether mixture to provide 4-(2-phenylthiophenyl)piperidine-4-carboxylic acid hydrobromide.

EXAMPLE 15

A mixture of 8 g of 4-(2-phenylthiophenyl)piperidine-4-carboxylic acid hydrobromide, Example 14, and 10 ml of acetic anhydride in 50 ml of pyridine is refluxed for 4 hours. Thereafter, the pyridine is removed by distillation in vacuo and the residue is triturated with 100 ml of 1 N hydrochloric acid. The residue is extracted thrice with portions of chloroform and the combined chloroform extracts are successively washed twice with water, dried, and concentrated. The residue is recrystallized from acetone to provide 1-acetyl-4-(2-phenylthiophenyl)piperidine-4-carboxylic acid.

EXAMPLE 16

A suspension of 3.4 g of 1-acetyl-4-(2-phenylthiophenyl)piperidine-4-carboxylic acid, Example 15, in 5 ml of freshly distilled thionyl chloride is warmed on a steam bath for 5 minutes, effecting a clear solution. The excess thionyl chloride is removed at 50° C. under reduced pressure. The residue is recrystallized from a benzene-cyclohexane mixture to provide 1-acetyl-4-(2-phenylthiophenyl)piperidine-4-carbonyl chloride.

EXAMPLE 17

A mixture of 2 g of 1-acetyl-4-(2-phenylthiophenyl)-piperidine-4-carbonyl chloride, Example 16, in 50 ml of absolute ethyl alcohol saturated with anhydrous chloride is stirred at reflux for 64 hours. Thereafter, the excess acid and alcohol is removed under reduced pressure, leaving a clear, glassy residue. The residue is dissolved in 30 ml of water and the aqueous solution is extracted with ethyl acetate. The aqueous solution is basified with potassium carbonate, liberating an oil. The oil is dissolved in ether and the ethereal solution is dried before concentrating to dryness, leaving a brownish oil. The oil, in ether, is converted to its oxalic acid salt which is recrystallized from a methyl alcohol-acetone-ether mixture to provide 4-ethoxycarbonyl-4-(2-phenylthiophenyl)-piperidine oxalate.

EXAMPLE 18

A mixture of 0.67 g of 4-ethoxycarbonyl-4-(2-phenylthiophenyl)piperidine, free base of Example 17, 0.48 g of 2-bromoethylbenzene, 0.65 g of sodium bicarbonate and 0.65 g of potassium iodide in 15 ml of dimethylformamide is stirred at 60°–70° C. for 16 hours. Thereafter, the mixture is diluted with ether and the diluted mixture is filtered. The filtrate is concentrated in vacuo. The residue is purified by column chromatography (alumina column, ether eluant) to provide a purified product which, in ether, is converted to its hydrobromic acid salt. The salt is recrystallized from an acetone-ether mixture to provide 4-ethoxycarbonyl-1-phenylethyl-4-(2-phenylthiophenyl)piperidine hydrobromide.

EXAMPLE 19

A mixture of 1.8 g of 4-ethylcarbonyl-4-(2-phenylthiophenyl)piperidine, free base of Example 11, 0.7 g of chloromethylcyclopropane, 1.6 g of sodium bicarbonate and 1.6 g of potassium iodide in dimethylformamide is stirred at 80°-85° C. for 16 hours. Thereafter, the mixture is permitted to cool to ambient temperature before being diluted with 50 ml of water. The diluted mixture is extracted thrice with 30 ml portions of ether. The combined ether extracts are sequentially washed with 25 ml of a saturated sodium chloride solution, dried over magnesium sulfate for 1 hour and the solvent removed. The residue is passed through an alumina absorption column packed in ether and eluted with a solution of 10% methyl alcohol in ether to provide the desired product, which is converted to its oxalic acid salt. Recrystallization from acetone-ether provides 1-cyclopropylmethyl-4-ethylcarbonyl-4-(2-phenylthiophenyl)-piperidine oxalate.

EXAMPLE 20

A mixture of 1.4 g of 4-ethoxycarbonyl-4-(2-phenylthiophenyl)piperdine, free base of Example 17, 0.52 g of chloromethylcyclopropane, 1.2 g of sodium bicarbonate and 1.2 g of potassium iodide in 15 ml of dimethylformamide is stirred for 16 hours at 80°-85° C. Thereafter, the mixture is permitted to cool before being diluted with 100 ml of water and then 200 ml of ether. Layers separate and the ether solution is dried and then evaporated. The residue is purified by chromatography (alumina column, ether eluant). The ether eluting solution is concentrated, providing a purified product which, in ether, is converted to its hydrobromic acid salt. The salt is recrystallized from an acetone-ether mixture to provide 1-cyclopropylmethyl-4-ethoxycarbonyl-4-(2-phenylthiophenyl) piperidine hydrobromide.

EXAMPLE 21

A mixture of 2.5 g of 4-cyano-1-methyl-4-(2-phenylthiophenyl)piperidine, free base of Example 3, and 1.7 g of phenyl chloroformate in 50 ml of methylene chloride is permitted to stand for 24 hours before being poured onto 100 g of ice. Thereafter, the mixture is extracted with 50 ml of methylene chloride and the organic solution is successively washed twice with 50 ml portions of water, washed once with 40 ml saturated sodium bicarbonate solution, washed once with 40 saturated sodium chloride solution, dried and evaporated. The residue is chromatographed through a silica gel column, first with an ether eluant and then with an ether-hexane (1:1) mixture eluant, until there is no indication of contamination by thin layer chromatography. Thereafter, the product is chromatographed through the same absorbent, ether eluant to provide 4-cyano-1-phenoxycarbonyl-4-(2-phenylthiophenyl)piperidine.

EXAMPLE 22

A mixture of 1.8 g of 4-ethylcarbonyl-4-(2-phenylthiophenyl)piperidine, free base of Example 11, 0.93 g of 2-chloromethyltetrahydrofuran, 1.6 g of sodium bicarbonate and 1.6 g of potassium iodide in 20 ml of dimethylformamide is stirred at 80°-85° C. for 16 hours. Thereafter, the mixture is permitted to cool before being diluted with 50 ml of water. The diluted mixture is extracted four times with 30 ml portions of ether and the combined ether extracts are washed with 25 ml saturated sodium chloride solution and then dried. The resulting oil product is chromatographed (alumina column, 10% methyl alcohol in ether eluant) to provide a purified product which, in ether, is converted to its oxalic acid salt. The salt is washed well with ether, dried under vacuum, recrystallized from a methanol-acetone-ether mixture and washed with ether to provide 4-ethylcarbonyl-4-(2-phenylthiophenyl)-1-(2-tetrahydrofurylmethyl)piperidine oxalate.

EXAMPLE 23

A mixture of 4-cyano-1-methyl-4-(2-phenylthiophenyl)-piperidine, free base of Example 3, in 15 ml of 48% hydrobromic acid is stirred at reflux for 16 hours. Thereafter, the excess acid is removed under reduced pressure, leaving a solid to which is added 10 ml of freshly distilled thionyl chloride. A clear solution results as the mixture is warmed on a steam bath. The excess thionyl chloride is distilled off, leaving a residue which is dissolved in 50 ml of absolute ethyl alcohol. The alcoholic solution is stirred at reflux for 1 hour and then permitted to stand for 16 hours. Then, the ethyl alcohol and any excess acid is removed under reduced pressure. The residue is dissolved in water and the aqueous solution is basified with dilute, ice cold sodium bicarbonate, liberating an amine which is dissolved in ether. The ethereal solution is dried before concentrating in vacuo. The residue, in ether, is converted to its hydrobromic acid salt which is recrystallized from a methyl alcohol-acetone-ether mixture to give 4-ethylcarbonyl-1-methyl-4-(2-phenylthiophenyl)piperidine hydrobromide.

EXAMPLE 24

A solution of 14.9 g of 1-methyl-4-cyano-4-[2-(4-chlorophenylthio)phenyl]piperidine, Example 1, in 75 ml of chloroform is added dropwise to a rapidly stirring mixture of 30.4 g of potassium carbonate and 7.6 g of cyanogen bromide in 80 ml of chloroform. After total addition, the reaction mixture is refluxed for 16 hours and then successively, filtered, washed thrice with 150 ml portions of water, washed once with 50 ml saturated sodium chloride solution and dried. The residue is dissolved in chloroform and the chloroform solution is chromatographed (silica gel F60, ether as eluant). The purified material is recrystallized from acetone to give 4-[2-(4-chlorophenylthio)phenyl]-1,4-dicyanopiperidine.

EXAMPLE 25

A mixture of 13.5 g of 4-[2-(4-chlorophenylthio)-phenyl]-1,4-dicyanopiperidine, Example 24, in 250 ml of 48% hydrobromic acid is stirred at 120° C. for 16 hours and then refluxed for three additional hours. Thereafter, the mixture is permitted to cool to ambient temperature. The resulting precipitate is sequentially collected by filtration, washed several times with water and dried. The solid is washed again three times with 100 ml portions of water and then dried to give 1-aminocarbonyl-4-[2-(4-chlorophenylthio)phenyl]piperidine-4-carboxylic acid.

EXAMPLE 26

A mixture of 1.1 g of 1-methyl-4-cyano-4-[2-(4-chlorophenylthio)phenyl]piperidine, free base of Example 1, in 25 ml of 48% hydrobromic acid is stirred at 130° C. for 16 hours. Thereafter, the reaction mixture is diluted with 175 ml of water before being rotary evaporated under reduced pressure at 85° C. The resulting solid is dissolved in water and the aqueous solution is chromatographed (Bio-Rad AG 50 W - X8 cation exchange resin column, 1.5-1.6 N ammonium hydroxide solution eluant) to provide a purified solid which is washed with water and then chloroform to give 4-[2-(4- chlorophenylthio)phenyl]-1-methylpiperidine-4-carboxylic acid.

EXAMPLE 27

A mixture of 1.8 g of 4-acetyl-4-(2-phenylthiophenyl)-piperidine, free base of Example 9, 0.75 g of 98% chloromethylcyclopropane, 1.7 g of sodium bicarbonate and 1.7 g of potassium iodide in 20 ml of dimethylformamide is stirred at 80°–85° C. for 16 hours. Thereafter, the mixture is cooled below ambient temperature before diluting with 50 ml of water. The aqueous solution is extracted four times with 30 ml portions of ether. The combined ether extracts are washed with 25 ml saturated sodium chloride solution and then dried. The residue is chromatographed (adsorption alumina column, 10% methyl alcohol eluant) to provide a purified product which is dissolved in ether and is converted to its oxalic salt, 4-acetyl-1-cyclopropylmethyl-4-(2-phenylthiophenyl)piperidine oxalate.

EXAMPLE 28

A mixture of 4.4 g of 4-cyano-4-[2-(4-fluorophenylthio)-phenyl]-1-methylpiperidine, Example 4, in 95 ml of 48% hydrobromic acid is stirred at reflux for 16 hours. Thereafter, the mixture is diluted with 300 ml of water before being rotary evaporated at 80° C. The resulting solid is swirled with 300 ml of water and dissolved by raising the pH to 9 with concentrated ammonium hydroxide. The solution is permitted to stand for 96 hours. The pH is slowly lowered to 4 with hydrochloric acid and then returned to 9 with concentrated ammonium hydroxide. The volume is reduced by rotary evaporation at 80° C. until a precipitate appears. Thereafter, the reaction mixture is cooled and the precipitate is collected by filtration and then washed with water. The precipitate is sequentially washed with acetone, treated with 1 ml of 48% hydrobromic acid diluted with 20 ml of water, applied to a Bio Rad AG 50 W - X8 cation exchange resin, and eluted with 5.8–8.7% ammonium hydroxide to provide 4-[2-(4-fluorophenylthio)-phenyl]-1-methylpiperidine-4-carboxylic acid.

EXAMPLE 29

A mixture of 19.8 g of 4-cyano-4-[2-(4-fluorophenylthio)-phenyl]-1-methylpiperidine, Example 5, in 200 ml of chloroform is added portionwise over a 15 minute span to a mixture of 33.4 g of of 97% cyanogen bromide and 130 g of potassium carbonate in 250 ml of chloroform. After total addition, the mixture is successively refluxed for 16 hours, cooled, filtered, washed thrice with 300 ml portions of water, once with 50 ml of saturated sodium chloride and dried. The residue is dissolved in benzene, decolorized with charcoal and filtered through celite. It is then concentrated and rediluted with hexane, effecting 1,4-dicyano-4-[2-(4-fluorophenylthio)phenyl]piperidine.

EXAMPLE 30

A solution of 2.0 g of 1,4-dicyano-4-[2-(4-fluorophenylthio)phenyl]piperidine, Example 29, in 12 ml of glacial acetic acid and 21 ml of 3 N hydrochloric acid is stirred at 110°–120° C. for 18 hours. Thereafter, the solution is diluted with 50 ml of water and the diluted solution is rotary evaporated twice to near dryness. The residual material is diluted in 100 ml of water and 2 ml of 58% ammonium hydroxide, giving a milky solution at pH 9. This aqueous suspension is extracted thrice with 150 ml portions of a benzene-ether (1:1) mixture. The combined extracts are washed, first with 50 ml of water and then with 25 ml saturated sodium chloride solution, and dried. The residual material is recrystallized from a benzene-hexane mixture to provide 4-cyano-4-[2-(4-fluorophenylthio)phenyl]piperidine.

EXAMPLE 31

A mixture of 12.0 g of 1,4-dicyano-4-[2-(4-fluorophenylthio)phenyl]piperidine, Example 29, in 240 ml of 48% hydrobromic acid is stirred in a 150° C. bath for 40 hours before adding 120 ml of glacial acetic acid and continuing the stirring at the same temperature for 30 additional hours. Thereafter, the solution is permitted to stand for 64 hours before the excess is distilled off. The residue is taken up in 50 ml of water and the aqueous mixture is rotary evaporated, leaving a solid which is washed with water and then ether. The resulting material is recrystallized three times from a methyl alcohol-ether mixture to provide 4-[2-(4-fluorophenylthio)-phenyl]piperidine-4-carboxylic acid hydrobromide.

EXAMPLE 32

A mixture of 0.7 g of 4-[2-(4-fluorophenylthio)-phenyl]-piperidine-4-carboxylic acid, free amino acid of Example 30, and 0.83 ml of acetic anhydride in 4.2 ml of pyridine is stirred at reflux for 4 hours. Thereafter, the excess pyridine is removed by rotary evaporation and the residue is taken up in 10 ml of water and treated with 10 ml of 1 N hydrochloric acid. The acidic mixture is extracted thrice with 20 ml portions of an ether-benzene (1:1) mixture and the combined extracts are successively washed twice with 40 ml portions of water, once with 15 ml of saturated sodium chloride solution and dried. The resulting product is recrystallized from acetone-ether to provide 1-acetyl-4-[2-(4-fluorophenylthio)phenyl]piperidine-4-carboxylic acid.

EXAMPLE 33

A mixture of 2.8 g of 4-ethoxycarbonyl-4-(2-phenylthiophenyl)piperidine, free base of Example 17, 1.2 g of allyl bromide, 2.5 g of sodium bicarbonate and a crystal of potassium iodide in 30 ml of dimethylformamide is stirred at 70°–80° C. for 16 hours. Thereafter, the mixture is diluted with water and ether, and the ether layer is separated and then dried. The ether is removed in vacuo and the resulting product is purified by passing through an alumina column, eluted with ether. The purified product is converted in ether to its oxalic acid salt. The salt is recrystallized from a methyl alcohol-acetone-ether mixture to provide 1-allyl-4-ethoxycarbonyl-4-(2-phenylthiophenyl)piperidine oxalate.

EXAMPLE 34

A mixture of 1.2 g of 4-[2-(4-chlorophenylthio)-phenyl]-1,4-dicyanopiperidine, Example 24, and 15 ml of a glacial acetic acid 3 N hydrochloric acid (1:2) solution is stirred at 110° C. for 24 hours. Thereafter, the solution is diluted with 80 ml of water before being evaporated to dryness. The solid residue is made strongly basic with ammonium hydroxide and the alkaline solution is extracted with ether. The combined ether extracts are successively dried, filtered and concentrated to dryness, leaving a white solid. The solid is dissolved in methylene chloride and this solution is chromatographed (silica gel/methylene chloride column, 10% methyl alcohol in methylene chloride as eluant). The desired fractions are concentrated to dryness. The resulting material is recrystallized from cyclohexane to provide 4-[2-(4-chlorophenylthio)phenyl]-4-cyanopiperidine.

EXAMPLE 35

A mixture of 1.5 g of 4-ethoxycarbonyl-4-(2-phenylthiophenyl)piperidine, free base of Example 17, 1.4 L g of γ-chloro-4-fluoroburtyrophenone ethylene ketal, 1.0 g of sodium bicarbonate and 1.5 g of potassium iodide in 15 ml of dimethylformamide is stirred at 70° C. for 16 hours. Thereafter, the mixture is diluted with water and ether. The ether layer is separated and then dried before being concentrated in vacuo, leaving 4-ethoxycarbonyl-1-[3-(4-fluorobenzoyl)propyl]-4-(2-phenylthiophenyl)-piperidine ethylene glycol ketal. The oil is stirred with 15 ml of ethyl alcohol and 15 ml of 3 N hydrochloric acid for 3 hours. Thereafter, the solution is permitted to cool before being basified with sodium hydroxide followed by extraction with ether. The combined ethereal extracts are passed through an alumina column; elution with ether provides a purified oil. The oil, in ether, is converted to its oxalic acid salt, which is recrystallized from an ethyl alcohol-ether mixture to provide 4-ethoxycarbonyl-1-[3-(4-fluorobenzoyl)propyl]-4-(2-phenylthiophenyl)piperidine oxalate.

EXAMPLE 36

A mixture of 1.8 g of 4-ethylcarbonyl-4-(2-phenylthiophenyl)piperidine, free base of Example 11, 1.9 g of γ-chloro-4-fluorobutyrophenone ethylene ketal, 1.6 g of sodium bicarbonate and 1.6 g of potassium iodide in dimethylformamide is stirred at 80°-85° C. for 16 hours. Thereafter, the mixture is permitted to cool to ambient temperature before being diluted with 50 ml of water and then extracted with ether. The pH of the aqueous phase is adjusted to 9-10 with 40% sodium hydroxide and the basified mixture is sequentially stirred for three hours and extracted twice with 30 ml portions of ether. The combined ether extracts are washed with 25 ml of saturated sodium chloride solution and then dried to provide an oil. The oil is stirred in a solution of 48 of absolute ethyl alcohol and 18 ml of 3 N hydrochloric acid for 21 hours. The pH of the alcoholic-acid solution is raised to 9-10 with 40% sodium hydroxide. The alkaline solution is extracted thrice with 30 ml portions of ether and the combined ether extracts are successively washed with 30 ml of saturated sodium chloride solution, dried and evaporated. The resulting product is chromatographed (alumina column, 10% methyl alcohol in ether mixture as eluant). The purified product, in ether, is converted to its oxalic acid salt. The salt is recrystallized from a chloroform-ether mixture to provide 4-ethylcarbonyl-1-[3-(4-fluorobenzoyl)propyl]-4-(2-phenylthiophenyl)piperidine oxalate.

We claim:

1. A compound of the formula

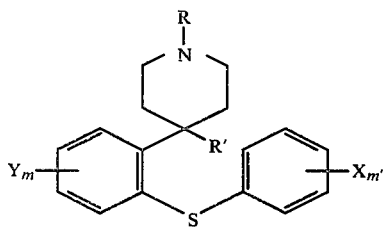

or a pharmaceutically acceptable acid addition salt thereof, in which R is hydrogen, loweralkyl, loweralkenyl, loweralkynyl, cycloalkylloweralkyl, phenylloweralkyl, loweralkanoyl, aminocarbonyl, phenoxycarbonyl, benzoylloweralkyl, cyano, ethylene glycol ketal of the formula

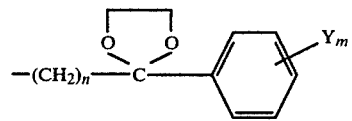

or tetrahydrofurylmethyl; R'0 is cyano, COOH, COZ, loweralkanoyl or loweralkoxycarbonyl; X and Y are the same or different and each can be hydrogen, chlorine, fluorine, bromine, methoxy, methylthio or trifluoromethyl; Z is chlorine, fluorine or bromine; m and m' are the same or different and each can be the integer 1 or 2; and n is an integer of 1 to 4, inclusive.

2. A compound as defined in claim 1 in which R is hydrogen, loweralkyl of from 1 to 3 carbon atoms, loweralkenyl of 3 or 4 carbon atoms, cycloalkylloweralkyl in which the cycloalkyl portion contains from 3 to 6, inclusive carbon atoms and the loweralkyl portion contains from 1 to 3, inclusive, carbon atoms, phenylloweralkyl in which the loweralkyl portion contains from 1 to 3, inclusive carbon atoms, loweralkanoyl, benzoylloweralkyl in which the loweralkyl portion contains from 1 to 3, inclusive, carbon atoms, cyano, ethylene glycol ketal of the formula

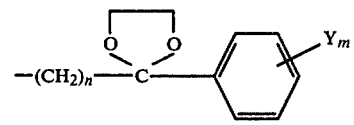

or tetrahydrofurylmethyl.

3. A compound defined in claim 2 in which Y is hydrogen.

4. A compound defined in claim 2 in which X is hydrogen, chlorine, fluorine or bromine.

5. A compound defined in claim 4 in which Y is hydrogen.

6. A compound defined in claim 1 in which R' is cyano, COOH, COZ, loweralkanoyl in which the loweralkyl portion contains from 1 to 3, inclusive, carbon atoms, or loweralkoxycarbonyl in which the loweralkoxy portion contains from 1 to 3, inclusive, carbon atoms.

7. A compound defined in claim 6 in which Y is hydrogen.

8. A compound defined in claim 6 in which X is hydrogen, chlorine, fluorine or bromine.

9. A compound defined in claim 8 in which Y is hydrogen.

10. A compound defined in claim 2 in which R' is cyano, COOH, COZ, loweralkanoyl in which the loweralkyl portion contains from 1 to 3, inclusive, carbon atoms, or loweralkoxycarbonyl in which the loweralkoxy portion contains from 1 to 3, inclusive, carbon atoms.

11. A compound defined in claim 10 in which Y is hydrogen.

12. A compound defined in claim 10 in which X is hydrogen, chlorine, fluorine or bromine.

13. A compound defined in claim 1 in which X is hydrogen.

14. A compound defined in claim 1 in which Y is hydrogen.

15. A compound defined in claim 1 in which X is hydrogen, chlorine, fluorine or bromine.

16. A compound defined in claim 15 in which Y is hydrogen.

17. The compound defined in claim 1 which is 4-[2-(4-chlorophenylthio)phenyl]-4-cyano-1-methylpiperidine.

18. The compound defined in claim 1 which is 4-[2-(4-chlorophenylthio)phenyl]-1-methylpiperidine-4-carboxylic acid.

19. The compound defined in claim 1 which is 4-cyano-1-methyl-4-(2-phenylthiophenyl)piperidine.

20. The compound defined in claim 1 which is 4-cyano-4-[2-(4-fluorophenylthio)phenyl]-1-methylpiperidine.

21. The compound defined in claim 1 which is 4-ethylcarbonyl-1-methyl-4-(2-phenylthiophenyl)piperidine.

22. The compound defined in claim 1 which is 4-acetyl-1-methyl-4-(2-phenylthiophenyl)piperidine.

23. The compound defined in claim 1 which is 1-methyl-4-propylcarbonyl-4-(2-phenylthiophenyl)piperidine.

24. The compound defined in claim 1 which is 4-acetyl-1-cyano-4-[2-phenylthiophenyl]piperidine.

25. The compound defined in claim 1 which is 4-acetyl-4-(2-phenylthiophenyl)piperidine.

26. The compound defined in claim 1 which is 1-cyano-4-ethylcarbonyl-4-(2-phenylthiophenyl)piperidine.

27. The compound defined in claim 1 which is 4-ethylcarbonyl-4-(2-phenylthiophenyl)piperidine.

28. The compound defined in claim 1 which is 4-ethylcarbonyl-1-phenethyl-4-(2-phenylthiophenyl)piperidine.

29. The compound defined in claim 1 which is 1,4-dicyano-4-(2-phenylthiophenyl)piperidine.

30. The compound defined in claim 1 which is 4-(2-phenylthiophenyl)piperidine-4-carboxylic acid.

31. The compound defined in claim 1 which is 1-acetyl-4-(2-phenylthiophenyl)piperidine-4-carboxylic acid.

32. The compound defined in claim 1 which is 1-acetyl-4-(2-phenylthiophenyl)piperidine-4-carbonyl chloride.

33. The compound defined in claim 1 which is 4-ethoxycarbonyl-4-(2-phenylthiophenyl)piperidine.

34. The compound defined in claim 1 which is 4-ethoxycarbonyl-1-phenethyl-4-(2-phenylthiophenyl)piperidine.

35. The compound defined in claim 1 which is 1-cyclopropylmethyl-4-ethylcarbonyl-4-(2-phenylthiophenyl)piperidine.

36. The compound defined in claim 1 which is 1-cyclopropylmethyl-4-ethoxycarbonyl-4-(2-phenylthiophenyl)piperidine.

37. The compound defined in claim 1 which is 4-cyano-1-phenoxycarbonyl-4-(2-phenylthiophenyl)piperidine.

38. The compound defined in claim 1 which is 4-ethylcarbonyl-4-(2-phenylthiophenyl)-1-(2-tetrahydrofurylmethyl)-piperidine.

39. The compound defined in claim 1 which is 4-[2-(4-chlorophenylthio)phenyl]-1,4-dicyanopiperidine.

40. The compound defined in claim 1 which is 1-aminocarbonyl-4-[2-(4-chlorophenylthio)phenyl]piperidine.

41. The compound defined in claim 1 which is 4-acetyl-1-cyclopropylmethyl-4-(2-phenylthiophenyl)piperidine.

42. The compound defined in claim 1 which is 4-[2-(4-fluorophenylthio)phenyl]-1-methylpiperidine-4-carboxylic acid.

43. The compound defined in claim 1 which is 1,4-dicyano-4-[2-(4-fluorophenylthio)phenyl]piperidine.

44. The compound defined in claim 1 which is 4-cyano-4-[2-(4-fluorophenylthio)phenyl]piperidine.

45. The compound defined in claim 1 which is 4-[2-(4-fluorophenylthio)phenyl]piperidine-4-carboxylic acid.

46. The compound defined in claim 1 which is 1-acetyl-4-[2-(4-fluorophenylthio)phenyl]piperidine-4-carboxylic acid.

47. The compound defined in claim 1 which is 1-allyl-4-ethoxycarbonyl-4-(2-phenylthiophenyl)piperidine.

48. The compound defined in claim 1 which is 4-[2-(4-chlorophenylthio)phenyl]-4-cyanopiperidine.

49. The compound defined in claim 1 which is 4-ethoxycarbonyl-1-[3-(4-fluorobenzoyl)propyl]-4-(2-phenylthiophenyl)piperidine ethylene glycol ketal.

50. The compound defined in claim 1 which is 4-ethoxycarbonyl-1-[3-(4-fluorobenzoyl)propyl]-4-(2-phenylthiophenyl)piperidine.

51. The compound defined in claim 1 which is 4-ethylcarbonyl-1-[3-(4-fluorobenzoyl)propyl]-4-(2-phenylthiophenyl)piperidine.

52. A method of treating pain in mammals which comprises administering to a patient an effective amount of a compound defined in claim 1.

53. A method of treating depression in mammals which comprises administering to a patient an effective amount of a compound defined in claim 1.

54. A method of treating convulsions in mammals which comprises administering to a patient an effective amount of a compound defined in claim 1.

55. A pharmaceutical composition for treating pain, depression or convulsions which comprises between 0.5 and 70% of a compound defined in claim 1 and a pharmaceutically acceptable carrier therefor.

56. A process for preparing a compound of the formula

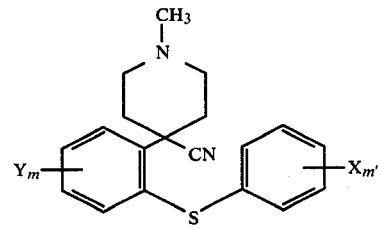

in which X and Y are the same or different and each can be hydrogen, chlorine, fluorine, bromine, methoxy, methylthio or trifluoromethyl and m and m' are the integer 1 or 2 which comprises treating a compound of the formula

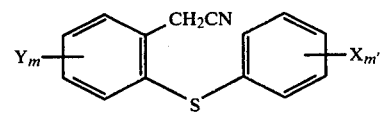

in which Y, X, m and m' are as defined earlier with mechlorethamine hydrochloride in the presence of a base at a temperature ranging from ambient to about 85° C.

57. A process for preparing a compound of the formula

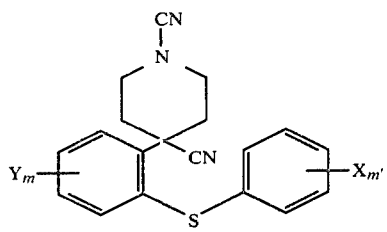

in which X and Y are the same or different and each can be hydrogen, chlorine, fluorine, bromine, methoxy, methylthio or trifluoromethyl and m and m' are the integer 1 or 2 which comprises treating a compound of the formula

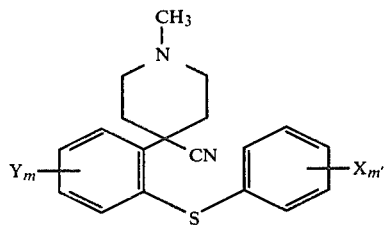

according to the first step of the Von Braun reaction, employing a solvent such as chloroform or methylene chloride, a mild acid scavenger such as potassium carbonate and a reaction temperature ranging from about ambient to reflux.

58. A process for preparing a compound of the formula

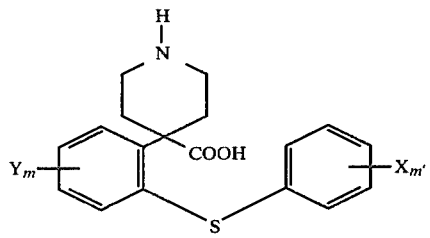

in which X and Y are the same or different and each can be hydrogen, chlorine, fluorine, bromine, methoxy, methylthio or trifluoromethyl and m and m' are the integer 1 or 2 which comprises subjecting to acid hydrolysis a compound of the formula

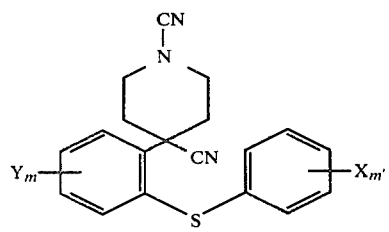

59. The process defined in claim 58 in which said hydrolysis is carried out with concentrated hydrobromic acid or a mixture of concentrated hydrobromic and glacial acetic acid at a temperature ranging from about 100° C. to reflux.

60. A process for preparing a compound of the formula

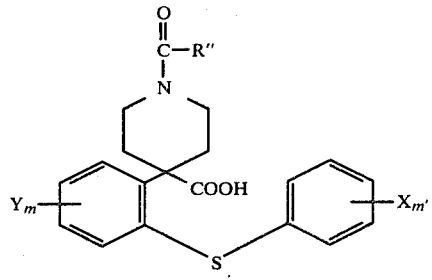

in which X and Y are the same or different and each can by hydrogen, chlorine, fluroine, bromine, methoxy, methylthio or trifluoromethyl and m and m' are the integer 1 or 2 and R" is loweralkyl which comprises acylating a compound of the formula

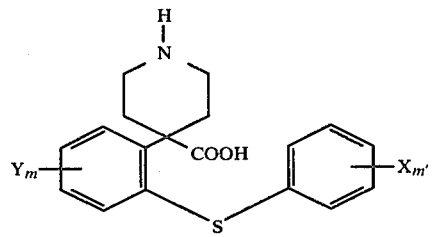

with an appropriate acyl halide of acyl anhydride.

61. The process defined in claim 60 in which the acylation is carried out in the presence of pyridine.

62. A process for preparing a compound of the formula

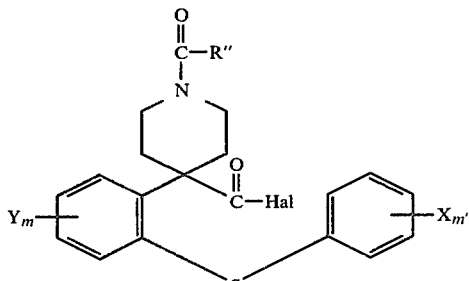

in which X and Y are the same or different and each can be hydrogen, chlorine, fluorine, bromine, methoxy, methylthio or trifluoromethyl; m and m' are the integer 1 or 2; R" is loweralkyl which comprises subjecting to displacement a compound of the formula

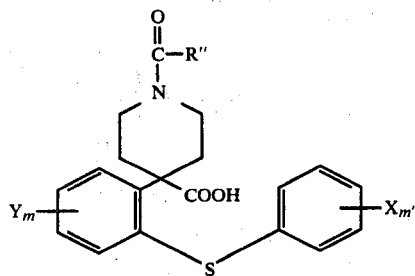

with an appropriate acid halide.

63. A process for preparing a compound of the formula

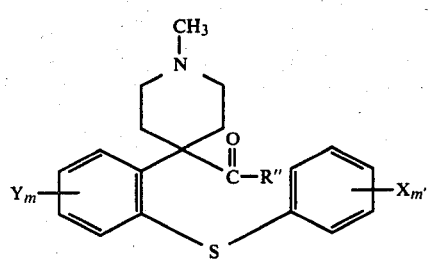

in which X and Y are the same or different and each can be hydrogen, chlorine, fluorine, bromine, methoxy, methylthio or trifluoromethyl; m and m' are the integer 1 or 2; and R" is loweralkyl which comprises treating a compound of the formula

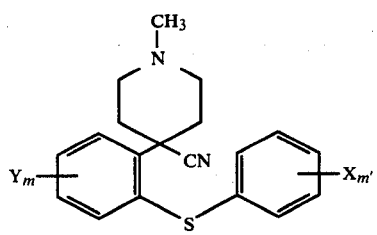

with a Grignard reagent of the formula R"MgHal in which R" is straight or branched chain loweralkyl and Hal is bromine or chlorine under Grignard reaction conditions.

64. A process for preparing a compound of the formula

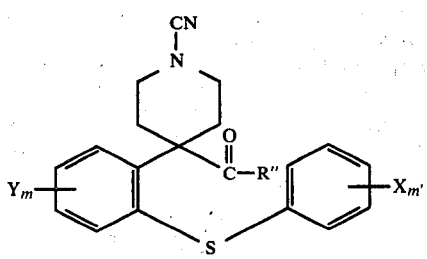

in which X and Y are the same or different and each can be hydrogen, chlorine, fluorine, bromine, methoxy, methylthio or trifluoromethyl; m and m' are the integer 1 or 2; and R" is loweralkyl which comprises treating a compound of the formula

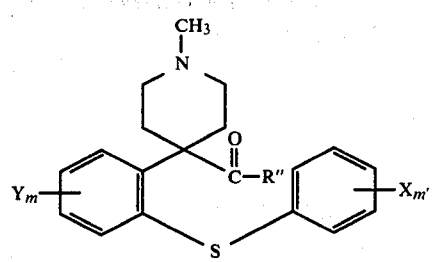

according to the first step of the Von Braun reaction including a solvent such as chloroform or methylene chloride, a mild acid scavenger such as potassium carbonate and a reaction temperature ranging from about ambient to reflux as reaction conditions.

65. A process for preparing a compound of the formula

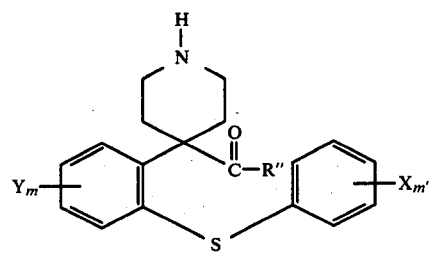

in which X and Y are the same or different and each can be hydrogen, chlorine, fluorine, bromine, methoxy, methylthio or trifluoromethyl; m and m' are the integer 1 or 2; R" is loweralkyl or CN which comprises subjecting to hydrolysis a compound of the formula

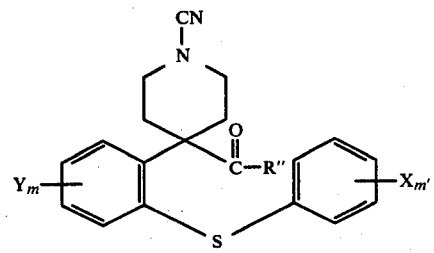

66. The process defined in claim 65 in which hydrolysis is carried out with a mild acid such as 2 N hydrochloric acid or a mixture of 2–3 N hydrochloric acid and glacial acetic acid and at a temperature ranging from about 90° C. to reflux.

67. A process for preparing a compound of the formula

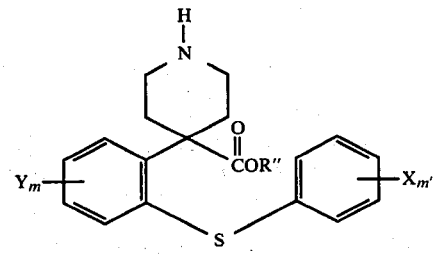

in which X and Y are the same or different and each can be hydrogen, chlorine, fluorine, bromine, methoxy, methylthio or trifluoromethyl; m and m' are the integer 1 or 2; and R" is loweralkyl which comprises esterifying a compound of the formula

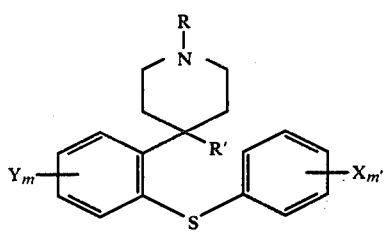

in which X, Y, m and m' and R are as defined earlier and R' is COZ in which Z is OH, chlorine, bromine or fluorine.

68. A process for preparing a compound of the formula

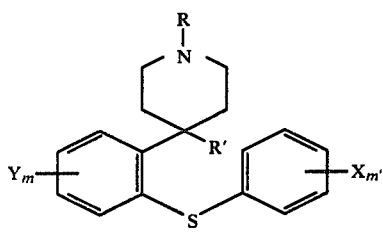

in which X and Y are the same or different and each can be hydrogen, chlorine, fluorine, bromine, methoxy, methylthio, trifluoromethyl and m and m' are the integer 1 or 2; R is loweralkyl, loweralkynyl, tetrahydrofurylmethyl, cycloalkylloweralkyl, phenylloweralkyl or ethylene glycol ketal of the formula

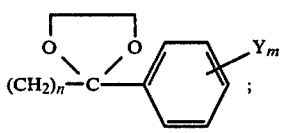

R' is loweralkanoyl or loweralkoxycarbonyl; and n is an integer between 1 and 4, inclusive, which comprises alkylating a compound of the formula

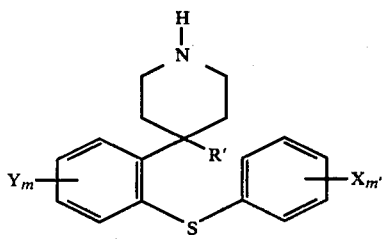

in which R' is CN, loweralkanoyl or loweralkoxycarbonyl with an appropriate alkylating agent.

69. The process defined in claim 68 in which the alkylation is carried out in the presence of a solvent such as dimethylformamide, an acid scavenger such as sodium bicarbonate and at a reaction temperature of from about 50° to 90° C.

70. The process defined in claim 69 further comprising the use of a reaction initiator such as potassium iodide.

71. A process for preparing a compound of the formula

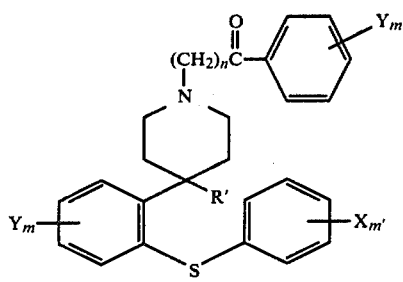

in which X and Y are the same or different and each can be hydrogen, chlorine, fluorine, bromine, methoxy, methylthio or trifluoromethyl; m and m' are the integer 1 or 2; n is an integer of from 1 to 4, inclusive; and R' is loweralkanoyl or loweralkoxycarbonyl which comprises subjecting to acid hydrolysis a compound of the formula

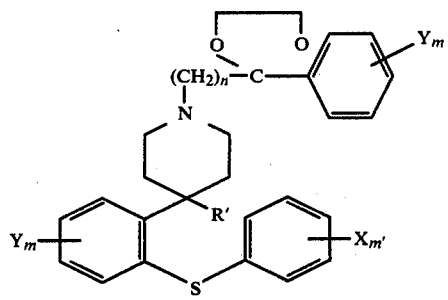

72. A process for preparing a compound of the formula

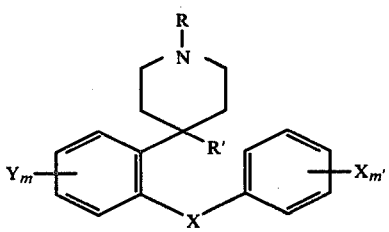

in which X and Y are the same or different and each can be hydrogen, chlorine, fluorine, bromine, methoxy, methylthio or trifluoromethyl; m and m' are the same or different and each can be the integer 1 or 2; R is hydrogen, loweralkyl, loweralkenyl, loweralkynyl, cycloalkylloweralkyl, phenylloweralkyl, loweralkanoyl, benzoylloweralkyl, cyano, ethylene glycol ketal of the formula

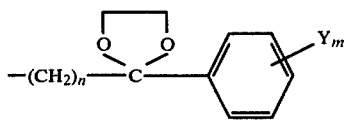

or tetrahydrofurylmethyl; and R' is loweralkanoyl or loweralkoxycarbonyl which comprises treating a compound of the formula

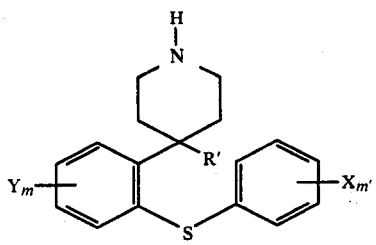

with an appropriate alkylating agent.

73. A process for preparing a compound of the formula

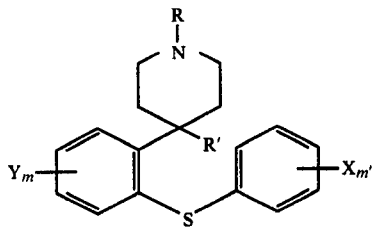

in which X and Y are the same or different and each can be hydrogen, chlorine, fluorine, bromine, methoxy, methylthio or trifluoromethyl; m and m' are the same or different and each can be the integer 1 or 2; R is loweralkyl, loweralkenyl, loweralkynyl, cycloalkylloweralkyl, phenylloweralkyl, loweralkanoyl, benzoylloweralkyl, cyano, ethylene glycol ketal of the formula

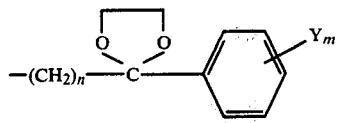

or tetrahydrofurylmethyl; and R' is COO loweralkyl which comprises esterifying a compound of the formula

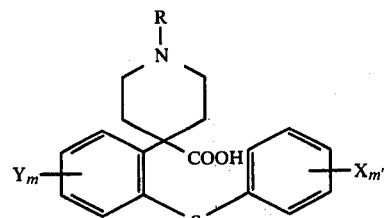

* * * * *

UNITED STATES PATENT AND TRADEMARK OFFICE
CERTIFICATE OF CORRECTION

PATENT NO. : 4,198,419
DATED : April 15, 1980
INVENTOR(S) : Ong et al.

It is certified that error appears in the above-identified patent and that said Letters Patent are hereby corrected as shown below:

Column 2, line 8, "writhin" should be --writhing--;
        line 35, "...o)-phenyl..." should be --...o)phenyl...--; and
        line 57, "methyl]-piperidine..." should be --...methyl]piperidine...--.
Column 3, line 14, "ad" should be --and--.
Column 4, line 21, "...phneyl..." should be --...phenyl...--; and
        line 68, "...phenyl)-piperidine..." should be --...phenyl)piperidine...--.

Column 5, line 50, "...$\overset{O}{\overset{\|}{C}}Z'$..." should be --...$\overset{O}{\overset{\|}{C}}Z$...--; and
        line 67, "...-4(2-phenyl..." should be --...-4-(2-phenyl...--.
Column 7, line 25, "$Y_m$" should be --$Y_m\rule{1cm}{0.4pt}$--.
Column 11, line 44, "...thio)-benzyl" should be --...thio)benzyl--.
Column 13, lines 19 and 65, "...phenyl)-piperidine..." should be --...phenyl)piperidine...--.
Column 14, line 46, "...phenyl)-piperidine..." should be --...phenyl)piperidine...--.
Column 15, line 14, "...phenyl)-piperidine..." should be --...phenyl)piperidine...--;
        line 31, "...thiophenyl) piperidine" should be --...thiophenyl)piperidine--; and
        line 42, "with 40 saturated" should be --with 40 ml saturated--.

UNITED STATES PATENT AND TRADEMARK OFFICE
CERTIFICATE OF CORRECTION

PATENT NO. : 4,198,419
DATED : April 15, 1980
INVENTOR(S) : Ong et al.

It is certified that error appears in the above-identified patent and that said Letters Patent are hereby corrected as shown below:

Column 16, line 6, "...phenyl)-piperidine..." should be
--...phenyl)piperidine...--.
Column 17, line 6, "...phenyl)-piperidine..." should be
--...phenyl)piperidine...--;
        lines 23 and 45, "...thio)-phenyl..." should be
--...thio)phenyl...--.
Column 18, line 24, "...phenyl]-piperidine..." should be
--...phenyl]piperidine...--.
Column 19, line 6, "1.4 Lg" should be --1.4 g--; and
        line 7, "...fluoroburtyrophenone" should be
--...fluorobutyrophenone--.
Column 20, line 11, "R'O is" should be --R' is--.
Column 21, line 63, "...methyl)-piperidine" should be
--...methyl)piperidine--.
Column 24, line 23, "fluroine" should be --fluorine--.

Signed and Sealed this

Twenty-fifth Day of November 1980

[SEAL]

Attest:

SIDNEY A. DIAMOND

Attesting Officer     Commissioner of Patents and Trademarks